(12) United States Patent
Veeraraghavan et al.

(10) Patent No.: US 8,030,446 B2
(45) Date of Patent: Oct. 4, 2011

(54) MUTANT PROLINE-AND-ARGININE RICH PEPTIDES AND METHODS FOR USING THE SAME

(75) Inventors: Sudha Veeraraghavan, Houston, TX (US); Michael Simons, Hanover, NJ (US)

(73) Assignees: Trustees of Dartmouth College, Hanover, NH (US); Board of Regents University of Texas System, Austin, TX (US)

( * ) Notice: Subject to any disclaimer, the term of this patent is extended or adjusted under 35 U.S.C. 154(b) by 1155 days.

(21) Appl. No.: 11/673,790

(22) Filed: Feb. 12, 2007

(65) Prior Publication Data
US 2009/0068736 A1    Mar. 12, 2009

Related U.S. Application Data

(60) Provisional application No. 60/772,092, filed on Feb. 10, 2006.

(51) Int. Cl.
*C07K 7/00* (2006.01)
(52) U.S. Cl. ........................ 530/327; 514/21.5; 514/21.6
(58) Field of Classification Search .................. 530/327; 514/21.5, 21.6
See application file for complete search history.

(56) References Cited

U.S. PATENT DOCUMENTS

| 4,504,469 | A | * | 3/1985 | Melin et al. | 514/11 |
| 4,704,692 | A | * | 11/1987 | Ladner | 703/11 |
| 5,013,657 | A | * | 5/1991 | Bryan et al. | 435/222 |
| 5,241,470 | A | * | 8/1993 | Lee et al. | 436/86 |
| 6,133,233 | A | | 10/2000 | Ross et al. | |
| 7,345,021 | B1 | * | 3/2008 | Simons et al. | 514/12 |
| 2006/0205645 | A1 | * | 9/2006 | Compernolle et al. | 514/12 |

OTHER PUBLICATIONS

Anbanandam, Asokan (Journal of Molecular Biology 384(1), 219-227, 2008).*
Bao et al., "PR-39 and PR-11 peptides inhibit ischemia-reperfusion injury by blocking proteasome-mediated IkaapaBetaAlpha degradation", Am J Physiol Heart Circ Physiol 2001 281:H2612-H2618.
Gaczynska et al., "Proline-and Arginine-Rich Peptides Constitute a Novel Class of Allosteric Inhibitors of Proteasome Activity", Biochemistry 2003 42:8663-8670.
Gao et al., "Inhibition of ubiquitin-proteasome pathway-mediated IkappaBetaAlpha degradation by a naturally occurring antibacterial peptide", J. Clin. Invest. 2000 106:439-448.

* cited by examiner

*Primary Examiner* — David Lukton
(74) *Attorney, Agent, or Firm* — Licata & Tyrrell, P.C.

(57) ABSTRACT

The present invention relates to mutant proline-and-arginine rich (PR) peptides with defined structural characteristics for use in inhibiting mammalian 20S proteasome activity and modulating expression of genes regulating the NF-κB pathway. Mutant PR peptides of the present invention differ from wild-type PR peptides by having at least one to three amino acid substitutions, wherein at least one of the amino acid residues at position one, two or three of the mutant PR peptide is positively charged.

9 Claims, 1 Drawing Sheet

MUTANT PROLINE-AND-ARGININE RICH PEPTIDES AND METHODS FOR USING THE SAME

This application claims benefit of U.S. Provisional Patent Application Ser. No. 60/772,092, filed Feb. 10, 2006, the content of which is incorporated herein by reference in its entirety.

This invention was made in the course of research sponsored by the National Institutes of Health (Grant No. RO1 HL70247). The U.S. government may have certain rights in this invention.

BACKGROUND OF THE INVENTION

Blood vessels grow in response to tissue injury and ischemia via angiogenesis, arteriogenesis and vasculogenesis. Transcriptional activation of a number of angiogenesis-related genes including VEGF, VEGF receptors such as flt-1 and neuropilin-1, and PDGF-B, and angiopoietin among others (Semenza (2000) *Biochem. Pharmacol.* 59:47-53) are regulated by hypoxia-inducible factor (HIF)-1α. Further, macrophages secrete numerous proteins including cytokines (IL-2 and TNF-α) and matrix metalloproteinases (Sunderkotter, et al. (1991) *Pharmacol. Ther.* 51:195-216; Gordon, et al. (1995) *Curr. Opin. Immunol.* 7:24-33; Arras, et al. (1998) *Basic Res. Cardiol.* 93:97-107). Among these is PR39, a cathelin-like "proline-and-arginine rich peptide" (PARP) originally isolated from pig intestine for its antimicrobial property (Agerberth, et al. (1996) *Vet. Immunol. Immunopathol.* 54:127-31; Agerberth, et al. (1991) *Eur. J. Biochem.* 202:849-54). PR39 and its homologs are found in the wound fluid of many animals as well as along the border of acute myocardial infarction (Gallo, et al. (1994) *Proc. Natl. Acad. Sci. USA* 91:11035-9). Secreted as a prepropeptide, the mature 39 amino acid C-terminal polypeptide chain (PR39) is produced by rapid cleavage of a canonical leader sequence (Gudmundsson, et al. (1995) *Proc. Natl. Acad. Sci. USA* 92:7085-9). PR39 crosses cell membranes readily, and is reported to bind to SH3 domains of cytosolic component of NADPH oxidase complex, protein $p47^{phox15}$ and a signaling adaptor protein $p130^{Cas9}$ (Gudmundsson, et al. (1995) supra; Chan & Gallo (1998) *J. Biol. Chem.* 273:28978-85; Chan, et al. (2001) *J. Invest. Dermatol.* 116:230-5).

PR39 is composed of 39 amino acids and induces angiogenesis and reduces inflammation in mouse models. PR39 is suggested to induce angiogenesis by acting along the VEGF and FGF pathway. PR39 also selectively inhibits the degradation of proteins including HIF-1α and IκBα, presumably by binding to the α7 subunit of the 20S proteasome. U.S. Patent Application Publication No. 20040009463 discloses a method for PR39 peptide-mediated selective inhibition of IκBα, and certain PR39-derived oligopeptides. A peptide composed of the first eleven amino acid residues of PR39, namely PR11, is also able to inhibit the 20S proteasome, albeit with a reduced $K_i$.

Studies have shown that PR39 stimulates angiogenesis in vitro and in vivo. Transgenic expression in cardiac myocytes results in increased vessel numbers and reduced coronary resistance (Li, et al. (2000) *Nat. Med.* 6:49-55). These effects appear to derive from the inhibition of HIF-1α degradation, which results in increased VEGF expression. PR39 also increases the expression of FGFR1 and syndecan-4, another FGF-2 signaling protein (Volk, et al. (1999) *J. Biol. Chem.* 274:24417-24; Li, et al. (1997) *Circ. Res.* 81:785-96), suggesting that PR39 may also induce angiogenesis via FGF pathway. PR39 appears to function by binding to the non-catalytic α7 subunit of 20S proteasome and inhibiting the degradation of another key intracellular protein, NF-κB inhibitor, IκBα (Gao, et al. (2000) *J. Clin. Invest.* 106:439-48).

Non-lysosomal degradation of cellular proteins occurs by the action of E1, E2 and E3 enzymes that result in the tetra-ubiquitinylation of target proteins and their proteolysis by the enzymatic activities residing within the central chamber of the 20S proteasomes. Ubiquitin and ubiquitin-like proteins are responsible for regulating numerous cellular pathways including the cell division cycle, transcription, protein sorting in the secretory pathway, membrane protein transport, endocytosis, nuclear transport, and signal transduction. The identification and analyses of inhibitors of proteasome are, therefore, of immense value to treat a variety of diseases, e.g., cancer, autoimmune diseases, muscle wasting, and inflammation. One example of a successful proteasome-based drug is the boronate, bortesomib (VELCADE™). This, and a variety of other agents currently in clinical testing act by blocking the enzymatic activities resident within the 20S proteasome resulting in the cessation of proteolysis of all substrate proteins and triggering apoptosis.

Cylindrical 20S proteasomes of eukaryotes, at approximately 700 kDalton mass, are composed of two heptameric inner rings of β-subunits and two heptameric outer rings of α-subunits. Thus, it is not surprising that a majority of proteasome inhibitors target the active sites that are exclusively associated with the β-subunits. The α-subunits are not known to possess proteolytic activity. It is remarkable, then, that the association of PARP with the α7 subunit of 20S proteasome should function to selectively inhibit proteolytic degradation of polypeptide chains such as IκBα. Atomic force microscopic investigations reveal that the 20S proteasome undergoes a gross structural change upon binding PR39. However, this does not sufficiently explain the mechanism of selective inhibition by PARP or the basis of PARP-proteasome interactions.

SUMMARY OF THE INVENTION

The present invention is an isolated mutant proline-and-arginine-rich (PR) peptide, wherein said peptide is 11 amino acid residues in length and has one to three amino acid substitutions in the amino acid sequence set forth in SEQ ID NO:2, wherein at least one of the amino acid residues at position one, two, or three is positively charged. In one embodiment, the mutant PR peptide further contains a C-terminal tryptophan. In another embodiment, at least two of the amino acid residues at positions one, two, or three are positively charged and the amino acid residue at position eight is not negatively charged. In a particular embodiment, the amino acid residue at position eight is hydrophobic. In still a further embodiment, the amino acid residue at position four is proline. Particular mutant PR peptides embraced by the present invention include PR peptides having the amino acid sequence set forth in SEQ ID NO:4 or SEQ ID NO:5.

Methods for using mutant PR peptides to inhibit mammalian 20S proteasome activity and modulate the expression of genes regulating the NF-κB pathway are also provided.

DETAILED DESCRIPTION OF THE INVENTION

Figure 1:
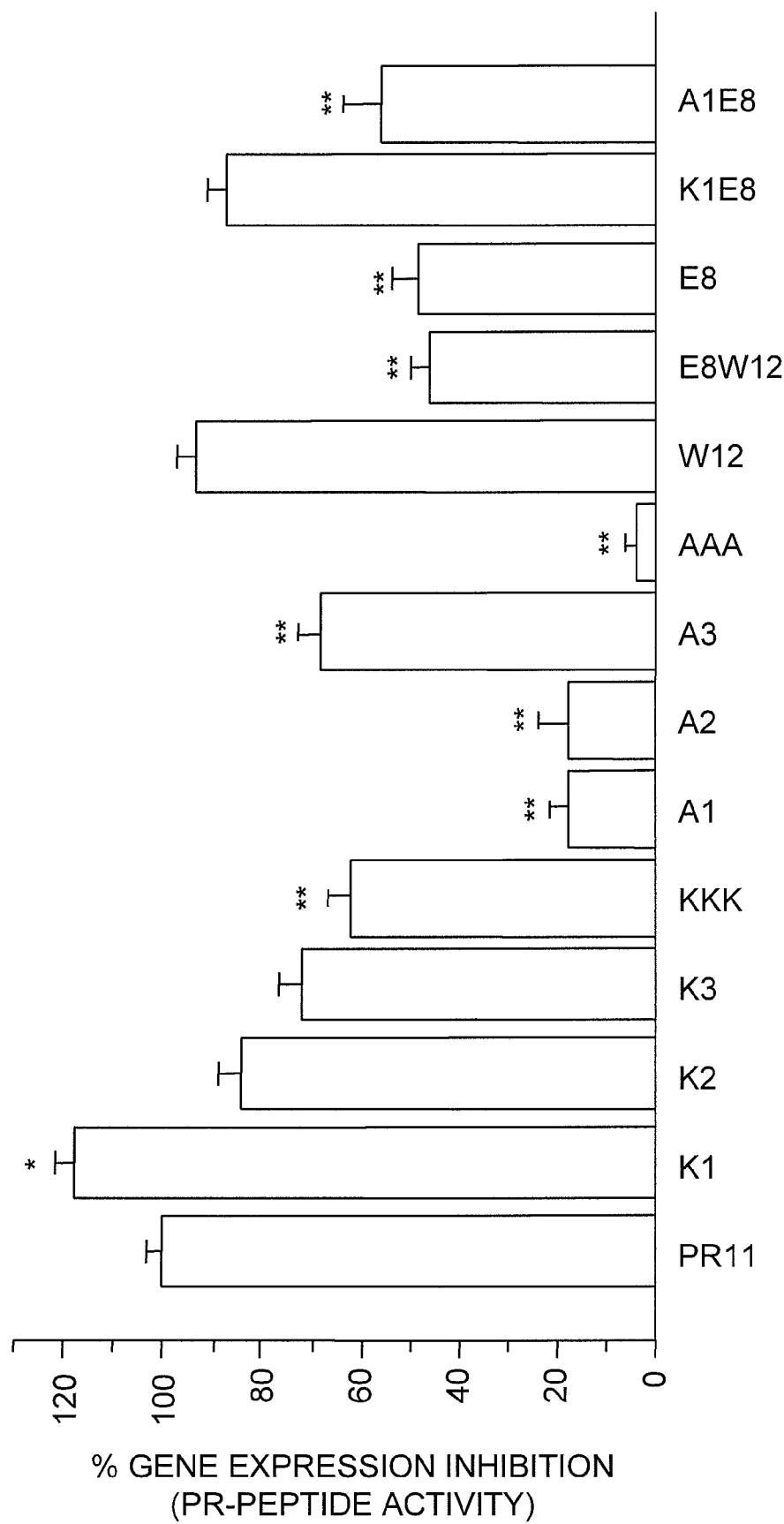
FIG. 1 shows the inhibitory effect of PR peptides on NF-κB pathway-related gene expression. Inhibitory effect was evaluated as averaged % inhibition over 13 down-regulated genes listed in Tables 5 and 6. PR mutant activity was reported to PR11 inhibitory effect, considered 100%; *p<0.05, **p<0.001 PR mutant vs. PR11.

The naturally occurring proline-and-arginine rich antibacterial peptide (PARP), PR39, and its truncated form, PR11, stimulate angiogenesis and inhibit inflammatory responses by selectively blocking the proteasomal degradation of IκBα and HIF-1α, respectively. Based upon structural and biochemical analysis of PR11 and mutants thereof, it has now been found that the 20S-inhibiting activity of PR peptides depends on the three-dimensional structure of the PR peptide. Furthermore, using microarray profiling, the link between peptide structure and activity was established for the NFκB pathway. Accordingly, the present invention pertains to novel mutant PR peptides which can be used to inhibit 20S proteasome activity as well as modulate the expression of genes regulating the NF-κB pathway. Moreover, based upon the identification of amino acid residues and three-dimensional structural characteristics of a PR peptide which are required for binding to the 20S proteasome and inhibiting the activity thereof, novel compounds can be designed which mimic the structure of the PR peptide and inhibit 20S proteasome activity.

In general, mutant PR peptides of the present invention are 10-12 amino acid residues in length and differ from the wild-type PR11 sequence (i.e., RRRPRPPYLPR; SEQ ID NO:2) by one to three amino acid residue substitutions. As used herein, the term peptide refers to a polymer of amino acid residues. The term peptide applies to naturally occurring amino acid polymers as well as amino acid polymers in which one or more amino acid residue is an artificial chemical analogue of a corresponding naturally occurring amino acid. The term peptide is also inclusive of modifications including, but not limited to, glycosylation, lipid attachment, sulfation, hydroxylation, methylation and the like.

A peptide of the present invention is isolated in the sense that it is substantially purified or essentially free from components that normally accompany or interact with the peptide as found in its naturally occurring environment. Thus, an isolated or purified peptide is substantially free of other cellular material, or culture medium when produced by recombinant techniques, or substantially free of chemical precursors or other chemicals when chemically synthesized.

A mutant PR peptide is intended to mean a peptide derived from the native or wild-type PR peptide sequence (i.e., SEQ ID NO:2) by substitution of one to at least three of the amino acid residues in the native peptide sequence or addition of one or more amino acids to the N-terminal and/or C-terminal end of the native PR peptide. While the present invention discloses mutant PR peptides of 10-12 amino acid residues in length, it is contemplated that one or more of the amino acid substitutions or additions disclosed herein can be incorporated into longer forms of known PARPs, e.g., PR15, PR39, etc. Accordingly, particular embodiments of the present invention embrace mutant PR peptides of about 10-40 amino acids in length.

Mutant PR peptides encompassed by the present invention are biologically active in that they continue to possess the desired biological activity of the native protein, that is, 20S proteasome inhibitory activity as described herein. Biologically active mutants of a native PR peptide of the invention will have at least about 70%, 75%, 80%, 85%, or desirably at least about 90% or more sequence identity to the amino acid sequence of the native peptide as determined by sequence alignment programs well-known in the art (e.g., CLUSTALW or DIALIGN). A biologically active mutant PR peptide of the invention can differ from the native PR peptide by as few as 1, 2, 3, 4, or 5 amino acid residues.

The peptides of the invention can be mutated by amino acid substitution, deletion or insertion. Methods for such manipulations are generally known in the art. For example, PR mutants can be prepared by incorporating mutations in the DNA encoding the native PR peptide. Methods for mutagenesis and nucleotide sequence alterations are well-known in the art. See, for example, Kunkel (1985) *Proc. Natl. Acad. Sci. USA* 82:488 492; Kunkel, et al. (1987) *Methods in Enzymol.* 154:367 382; U.S. Pat. No. 4,873,192; Walker and Gaastra, eds. (1983) *Techniques in Molecular Biology*, MacMillan Publishing Company, New York. As another specific example, classical site-directed mutagenesis, e.g. QUICK-CHANGE™ commercially available from STRATAGENE® can be used to generate mutant PR peptides. Guidance as to appropriate amino acid substitutions that do not affect biological activity of the PR peptide are disclosed herein. In particular, as few as one positively charged amino acid residue at positions one to three of a PR peptide retains the biological activity of the PR peptide. Furthermore, 20S proteasome inhibitory activity is attributed to the presence of at least two positively charged amino acid residues at positions one to three and absence of a negatively charged amino acid residue at position eight. Moreover, the addition of a C-terminal tryptophan can increase the inhibitory activity of a PR11 peptide, whereas the presence of a hydrophobic amino acid side chain at position eight is preferred. In addition, Pro4 contributes to the 20S inhibiting activity of a PR peptide by providing structural rigidity or appropriate orientation to residues in the N-terminal half of the molecule. Accordingly, embodiments of the present invention embrace mutant PR peptides provided in Table 2.

To achieve an $I_{50}$ below 1.0 μM, particular embodiments embrace a PR mutant peptide having an amino acid sequence of $Xaa_1$-$(Xaa_2)_3$-Pro-Arg-Pro-$Xaa_3$-$Xaa_4$-$(Xaa_5)_{2-3}$-$Xaa_6$ (SEQ ID NO:29), wherein $Xaa_1$ is absent or Lys; $Xaa_2$ is any amino acid residue with the proviso that at least one of $Xaa_2$ is a positively charged amino acid residue; $Xaa_3$ is any amino acid residue; $Xaa_4$ is not a negatively charged amino acid residue; $Xaa_5$ is any amino acid residue; and $Xaa_6$ is absent or Trp.

As known to one of skill in the art, amino acids can be placed into three main classes: hydrophilic amino acids, hydrophobic amino acids and cysteine-like amino acids, depending primarily on the characteristics of the amino acid side chain. These main classes can be further divided into subclasses. Hydrophilic amino acids include amino acids having acidic, basic or polar side chains and hydrophobic amino acids include amino acids having aromatic or apolar side chains. Apolar amino acids can be further subdivided to include, among others, aliphatic amino acids.

A hydrophobic amino acid refers to an amino acid having a side chain that is uncharged at physiological pH and that is repelled by aqueous solution. Examples of genetically encoded hydrophobic amino acids include Ile, Leu, and Val. Examples of non-genetically encoded hydrophobic amino acids include t-BuA. Aromatic amino acids refer to hydrophobic amino acid residues having a side chain containing at least one ring having a conjugated pi-electron system (aromatic group). The aromatic group can be further substituted with substituent groups such as alkyl, alkenyl, alkynyl, hydroxyl, sulfonyl, nitro and amino groups, as well as others. Examples of genetically encoded aromatic amino acids include Phe, Tyr and Trp. Commonly encountered non-genetically encoded aromatic amino acids include phenylglycine, 2-naphthylalanine, beta-2-thienylalanine, 1,2,3,4-tetrahydroisoquinoline-3-carboxylic acid, 4-chlorophenylalanine, 2-fluorophenylalanine, 3-fluorophenylalanine and 4-fluorophenylalanine. An apolar amino acid residue refers to a hydrophobic amino acid having a side chain that is generally uncharged at physiological pH and that is not polar. Examples of genetically encoded apolar amino acids include Gly, Pro and Met. Examples of non-encoded apolar amino acids include Cha. An aliphatic amino acid residue refers to an apolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

Hydrophilic amino acid residues refer to amino acid residues having a side chain that is attracted by aqueous solution. Examples of genetically encoded hydrophilic amino acids include Ser and Lys. Examples of non-encoded hydrophilic amino acids include Cit and hCys. Acidic amino acid residues refer to hydrophilic amino acids having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate). A basic amino acid residue refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include the non-cyclic amino acids ornithine, 2,3-diaminoproprionic acid, 2,4-diaminobutyric acid and homoarginine. A polar amino acid refers to a hydrophilic amino acid having a side chain that is uncharged at physiological pH, but which has a bond in which the pair of electrons shared in common by two atoms is held more closely by one of the atoms. Examples of genetically encoded polar amino acids include asparagine and glutamine. Examples of non-genetically encoded polar amino acids include citrulline, N-acetyl lysine and methionine sulfoxide.

As will be appreciated by those having skill in the art, the above classifications are not absolute. Several amino acids exhibit more than one characteristic property, and can therefore be included in more than one category. For example, tyrosine has both an aromatic ring and a polar hydroxyl group. Thus, tyrosine has dual properties and can be included in both the aromatic and polar categories. Similarly, in addition to being able to form disulfide linkages, cysteine also has apolar character. Thus, while not strictly classified as a hydrophobic or apolar amino acid, in many instances cysteine can be used to confer hydrophobicity to a peptide.

Certain commonly encountered amino acids which are not genetically encoded and which can be present, or substituted for an amino acid, in the peptides of the invention include, but are not limited to, beta-alanine (β-Ala) and other omega-amino acids such as 3-aminopropionic acid (Dap), 2,3-diaminoproprionic acid (Dpr), 4-aminobutyric acid and so forth; alpha-aminoisobutyric acid (Aib); epsilon-aminohexanoic acid (Aha); delta-aminovalieric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe (pNH$_2$)); N-methyl valine (MeVal); homocysteine (hCys) and homoserine (hSer). These amino acids also fall into the categories defined above.

The classifications of the above-described genetically encoded and non-encoded amino acids as they relate to the present PR peptides are summarized in Table 1. It is to be understood that Table 1 is for illustrative purposes only and does not purport to be an exhaustive list of amino acid residues that may be used in the PR peptides described herein. Other amino acid residues that are useful for making the peptides described herein can be found, e.g., in Fasman (1989) CRC Practical Handbook of Biochemistry and Molecular Biology, CRC Press, Inc. Amino acids not specifically mentioned herein can be conveniently classified into the above-described categories on the basis of known behavior and/or their characteristic chemical and/or physical properties as compared with amino acids specifically identified.

TABLE 1

| Classification | Genetically Encoded |
|---|---|
| Positively Charged | Lys, Arg, His |
| Negatively Charged | Asp, Glu |
| Hydrophobic | Gly, Ala, Val, Leu, Ile, Pro, Met, Phe, Trp, |

A mutant PR peptide of the invention can be prepared using any suitable recombinant or chemical synthesis method. For example, the availability of nucleic acid molecules encoding PR peptides enables production of mutant PR peptides of the invention using cell-based and cell-free systems. Accordingly, particular embodiments, of the present invention embrace nucleic acid molecules encoding mutant PR peptides disclosed herein as well as vectors and hosts harboring such nucleic acid molecules.

Cell-free translation methods are well-known in the art. For example, a cDNA or gene can be cloned into an appropriate transcription vector for in vitro transcription, followed by cell-free translation in a suitable cell-free translation system. In vitro transcription and translation systems are commercially available, e.g., from PROMEGA® Biotech, Madison, Wis., or GIBCO-BRL®, Rockville, Md.

Larger quantities of mutant PR peptide can be produced by in vitro expression in a suitable prokaryotic or eukaryotic system. Suitable vectors for recombinant protein expression in mammalian, yeast, or prokaryotic systems are commercially available from such sources as STRATAGENE®, INVITROGEN™, Pharmacia and the like.

When the nucleic acid molecules of the invention are used for production of a mutant PR peptide in vitro, in vivo or ex vivo, the nucleic acid molecule can include the coding sequence for the mature mutant PR peptide by itself; or the coding sequence for the mature mutant PR peptide in-frame with other coding sequences, such as those encoding a leader or secretory sequence, a pre-, or pro- or prepropeptide sequence, or other fusion protein. An exemplary prepropeptide sequence is METQRASLCLGRWSLWLLLLGLVVP-SASAQ ALSYREAVLRAVDRLNEQSSEANLYRL-LELDQPPKADEDPGTPKPVSFTVKETVCPRPT R QPPELCDFKENGRVKQCVGTVTLNPSIH-SLDISCNEIQSV (SEQ ID NO:30) and an exemplary propeptide sequence is QALSYREAVLRAVDRLNEQS SEANLYRLLELDQPPKADEDPGTPKPVS-

FTVKETVCPRPTRQPPELCDFKENGRVKQCVGTVTLNPSIHSLDISCNEIQSV (SEQ ID NO:31).

Protein sequences which facilitate purification of a mutant PR peptide can also be encoded by an expression vector. The nucleic acid molecule encoding a mutant PR peptide can further contain non-coding 5' and 3' sequences, such as transcribed, non-translated sequences, splicing and polyadenylation signals, ribosome binding sites and sequences that stabilize mRNA. Such sequences are well-known to the skilled artisan and can be obtained from the PR39 locus or from another unrelated gene.

Nucleic acid molecules of the present invention can be maintained in vitro as DNA in any convenient cloning vector, e.g., in plasmid cloning/expression vector, to produce large quantities of a substantially pure mutant PR peptide. An expression vector harboring a nucleic acid encoding a mutant PR peptide generally contain all the necessary regulatory sequences, for example, promoter and terminator sequences, operably linked to the nucleic acid encoding a mutant PR peptide such that the mutant PR peptide coding sequence is transcribed into RNA and subsequently translated into protein. Large numbers of suitable vectors and regulatory sequences are known to those of skill in the art, and are commercially available. The following vectors are provided by way of example, bacterial vectors pQE70, pQE60, pQE-9 (QIAGEN®), pBS, pD10, pBLUESCRIPT® SK, pBSKS, pNH8A, pNHI8A, pNH46A (STRATAGENE®) and pRIT5 (Pharmacia); and eukaryotic vectors pWLNEO, pSV2CAT, pOG44, pXT1, pSG (STRATAGENE®) pSVK3, pBPV, pMSG, pSVL (Pharmacia). As further examples, a mutant PR peptide cDNA can be inserted in the pEF/myc/cyto vector (INVITROGEN™) or the pCMV-Tag3b vector (STRATAGENE®) and transformed (e.g., calcium phosphate transfection, DEAE-dextran-mediated transfection, microinjection, cationic lipid-mediated transfection, electroporation) into HeLa thereby facilitating purification and use of a mutant PR peptide.

However, any other plasmid or vector can be used as long as they are replicable and viable in a host. In addition, a complete mammalian transcription unit and a selectable marker can be inserted into a prokaryotic plasmid for use in in vivo procedures. The resulting vector is then amplified in bacteria before being transfected into cultured mammalian cells or delivered directly to a subject with an acceptable carrier. Examples of vectors of this type include pTK2, pHyg and pRSVneo. Hence, these plasmids, constructs and vectors can be used in both in vitro and in vivo procedures.

Representative examples of appropriate hosts for in vitro procedures include bacterial cells, such as streptococci, staphylococci, *E. coli, Streptomyces* and *Bacillus subtilis* cells; fungal cells, such as yeast cells and *Aspergillus* cells, insect cells such as *Drosophila* S2 and *Spodoptera* Sf9 cells; animal cells such as CHO, COS, HeLa, C127, 3T3, BHK, and HEK 293 cells, and plant cells. When the nucleic acid encoding a mutant PR peptide encodes a prepropeptide or propeptide sequence, it can be particularly advantageous that a neutrophil, bone marrow, endothelial cell, or small intestine cell or cell line be used for recombinant peptide production for proper processing and secretion of a mature PR peptide (Shi, et al. (1994) *J. Leukoc. Biol.* 56(6):807-11; Li, et al. (2000) *Nat. Med.* 5:49-55; Storici and Zanetti (1993) *Biochem. Biophys. Res. Commun.* 196 (3):1058-1065). The selection of an appropriate host is deemed to be within the scope of those skilled in the art from the teachings herein.

An expression vector harboring a nucleic acid encoding a mutant PR peptide can also be used for in vivo or ex vivo therapeutic expression (i.e., gene therapy). Such a gene transfer vector includes, but is not limited to, a naked plasmid, a viral vector, such as an adenovirus, an adeno-associated virus, a herpes-simplex virus based vector, a lentivirus vector such as those based on the human immunodeficiency virus (HIV), a vaccinia virus vector, a synthetic vector for gene therapy, and the like (see Miller and Rosman (1992) *BioTechniques* 7:980-990; Anderson, et al. (1998) *Nature* 392:25-30; Verma and Somia (1997) *Nature* 389:239-242; Wilson (1996) *New Engl. J. Med.* 334:1185-1187; Suhr, et al. (1993) *Arch. Neurol.* 50:1252-1268). For example, a gene transfer vector employed herein can be a retroviral vector. Retroviral vectors contemplated for use herein are gene transfer plasmids that have an expression construct, i.e., a nucleic acid encoding a mutant PR peptide operatively linked to an appropriate promoter and terminator sequence, residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WO 92/07573, WO 90/06997, WO 89/05345, WO 92/05266 and WO 92/14829. These documents provide a description of methods for efficiently introducing nucleic acids into human cells using such retroviral vectors. Other retroviral vectors include, for example, mouse mammary tumor virus vectors (e.g., Shackleford, et al. (1988) *Proc. Natl. Acad. Sci. USA* 85:9655-9659), human immunodeficiency virus (e.g., Naldini, et al. (1996) *Science* 272:165-320), and the like.

Various procedures are also well-known in the art for providing helper cells that produce retroviral vector particles that are essentially free of replicating virus. See, for example, U.S. Pat. No. 4,650,764; Miller (1990) *Human Gene Therapy* 1:5-14; Markowitz, et al. (1988) *J. Virol.* 61(4):1120-1124; Watanabe, et al. (1983) *Mol. Cell. Biol.* 3(12):2241-2249; Danos, et al. (1988) *Proc. Natl. Acad. Sci. USA,* 85:6460-6464; and Bosselman, et al. (1987) *Mol. Cell. Biol.* 7(5): 1797-1806, which disclose procedures for producing viral vectors and helper cells that minimize the chances for producing a viral vector that includes a replicating virus.

For ex vivo applications, adult bone marrow cells can be obtained from the subject being treated and grown under suitable culture conditions in a container for a period of time sufficient to promote production by the bone marrow of early attaching cells. The early attaching cells are transfected in culture with a vector as described herein containing a nucleic acid encoding a mutant PR peptide and the transfected early attaching cells (and/or medium in which they are cultured after transfection) are then directly administered to a desired site in the subject so as to deliver to the site the expressed mutant PR peptide. Advantageously, transfected cells for ex vivo therapy can secrete the mutant PR peptide to effect non-transfected cells at the site of infusion.

Depending on the gene transfer vector selected and the mode of administration, a nucleic acid encoding a mutant PR peptide can be operatively linked to a variety of promoters to control initiation of mRNA transcription. Such promoters typically contain at least a minimal promoter in combination with a regulatory element which mediates temporal and/or spatial expression. When constitutive high-level expression is desired, a constitutive promoter such as CMV immediate early, HSV thymidine kinase, early and late SV40 can be selected.

As an alternative to viral-mediated transduction of host cells, therapeutic nucleic acids can be delivered to target cells via basic transfection methods such as permeabilizing the cell membrane physically or chemically. Liposomes or protein conjugates formed with certain lipids and amphophilic peptides can also be used for transfection (Stewart, et al. (1992) *Hum. Gene Ther.* 3(3):267-75; Zhu, et al. (1993) *Science* 261(5118):209-11). Such an approach is desirable when naked DNA or plasmid vectors are employed for expressing a mutant PR peptide.

In addition to therapeutic uses and recombinant protein production, vectors and host cells disclosed herein are useful for producing transgenic animals which overexpress a mutant PR peptide.

A mutant PR peptide produced by cell-free transcription/translation or by gene expression in a recombinant prokaryotic or eukaryotic system can be purified according to methods known in the art (e.g., fractionation on immunoaffinity or ion-exchange columns; ethanol precipitation; reverse phase HPLC; chromatography on silica or on a cation-exchange resin such as DEAE; chromatofocusing; SDS-PAGE; ammonium sulfate precipitation; or gel filtration using, for example, SEPHADEX® G-75).

Alternatively, a synthetic mutant PR peptide can be prepared using various synthetic methods of peptide synthesis via condensation of one or more amino acid residues, in accordance with conventional peptide synthesis methods. For example, peptides are synthesized according to standard solid-phase methodologies, such as may be performed on an APPLIED BIOSYSTEMS™ Model 430A peptide synthesizer (APPLIED BIOSYSTEMS™, Foster City, Calif.), according to manufacturer's instructions. Other methods of synthesizing peptides, either by solid phase methodologies or in liquid phase, are well-known to those skilled in the art.

A mutant PR peptide of the present invention can be used in in vitro, ex vivo or in vivo methods for inhibiting mammalian 20S proteasome activity or modulating expression of genes regulating the NF-κB pathway. Such methods involve contacting a cell with an effective amount of a mutant PR peptide (or expression vector encoding a mutant PR peptide) so that mammalian 20S proteasome activity is inhibited or the expression of genes regulating the NF-κB pathway is modulated. An effective amount of a PR peptide is an amount which results in a detectable change in the activity being targeted (i.e., mammalian 20S proteasome activity or expression of genes regulating the NF-κB pathway) in the cell as compared to a cell not contacted with the PR peptide. As the skilled artisan will appreciate, mammalian 20S proteasome activity can be monitored using any suitable assay including the chymotrypsin-like peptidase assay disclosed herein. Likewise, one or more of the genes disclosed in Tables 5-7 can be monitored to determine whether the mutant PR peptide is modulating the expression of a gene which regulates the NF-κB pathway.

When used in vivo, it is desirable that the mutant PR peptide is formulated into a pharmaceutically acceptable composition and administered to a subject in need of treatment (e.g., a subject in need of angiogenesis stimulation or inhibition of an inflammatory response) thereby ameliorating or inhibiting one or more symptoms associated with the disease or disease or condition being treated in the subject. Diseases or conditions which can be treated using the PR peptides of the present invention include, but are not limited to, wounding, autoimmune diseases, muscle wasting, inflammation, cancer, and other cardiovascular diseases.

Advantageously, mature PR peptides rapidly enter cells (Chan, et al. (1998) supra) and therefore a mutant PR peptide can be formulated with any suitable pharmaceutically acceptable carrier or excipient, such as buffered saline; a polyol (e.g., glycerol, propylene glycol, liquid polyethylene glycol and the like); carbohydrates such as glucose, mannose, sucrose or dextrans, mannitol; amino acids such as glycine; antioxidants; chelating agents such as EDTA or glutathione; preservatives or suitable mixtures thereof. In addition, a pharmaceutically acceptable carrier can include any solvent, dispersion medium, and the like which may be appropriate for a desired route of administration of the composition. The use of sustained-release delivery systems such as those disclosed by Silvestry, et al. ((1998) *Eur. Heart J.* 19 Suppl. I:I8-14) and Langtry, et al. ((1997) *Drugs* 53 (5): 867-84), for example, are also contemplated. The use of such carriers for pharmaceutically active substances is known in the art. Suitable carriers and their formulation are described, for example, in Remington: The Science and Practice of Pharmacy, Alfonso R. Gennaro, editor, 20th ed. Lippincott Williams & Wilkins: Philadelphia, Pa., 2000.

For therapeutic applications, mutant PR peptides or expression vector encoding a mutant PR peptide can be administered to a subject via various routes. For example, such administration can be carried out by inhalation or insufflation (either through the mouth or the nose), oral, buccal, parenteral, implantation (e.g., subcutaneously or intramuscularly), or directly infused into the myocardium (e.g., via a catheter). The mutant PR peptide can be administered continuously or intermittently (e.g., every couple of days, weeks, or months) to achieve the desired effect for an extended period of time.

For oral administration, the pharmaceutical compositions can take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well-known in the art. Liquid preparations for oral administration can take the form of, for example, solutions, syrups or suspensions, or they can be presented as a dry product for constitution with water or other suitable vehicle before use. Preparations for oral administration can be suitably formulated to give controlled release of the active agent. For buccal administration the compositions can take the form of tablets or lozenges formulated in conventional manner.

For administration by inhalation, a mutant PR peptide is conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin for use in an inhaler or insufflator can be formulated containing a powder mix of the compound and a suitable powder base such as lactose or starch.

A mutant PR peptide can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing or dispersing agents. Alternatively, the mutant PR peptide can be in powder form for constitution with a suitable vehicle, e.g., sterile pyrogen-free water, before use.

In addition, a mutant PR peptide can also be formulated as a depot preparation. Such long acting formulations can be administered by implantation (for example, subcutaneously or intramuscularly) or by intramuscular injection. Thus, for example, a mutant PR peptide can be formulated with suitable polymeric or hydrophobic materials (for example as an emulsion in an acceptable oil) or ion exchange resins, or as sparingly soluble derivatives, for example, as a sparingly soluble salt.

Toxicity and therapeutic efficacy of a selected mutant PR peptide or expression vector encoding a mutant PR peptide can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). For any mutant PR peptide used in the methods of the invention, the therapeutically effective dose can be estimated initially from animal models to achieve a concentration range that includes the $IC_{50}$ (i.e., the concentration of the mutant PR peptide, which achieves a half-maximal inhibition of signs or symptoms of the disease or condition be treated). Such information can be used to accurately determine useful doses in humans. For example, a typical daily dose of a mutant PR peptide may range from about 1 µg/kg to about 100 mg/kg of patient body weight or more per day, depending on the factors mentioned above.

Having identified the three-dimensional structure of the PR peptide, the present invention also provides methods for identifying agents which mimic the structure of the wild-type PR peptide. In accordance with this embodiment of the present invention, the structure of the PR peptide as disclosed in Table 3 can be used in molecular design techniques to computationally screen small molecule databases for chemical entities or compounds that bind to the 20S proteasome in a manner analogous to the PR peptide. Initially effector compounds can be selected for their structural similarity to the native PR peptide or a mutant PR peptide. The structural analog thus designed can then be modified by computer modeling programs to better define the most likely effective candidates. Reduction of the number of potential candidates is useful as it may not be possible to synthesize and screen a countless number of compound variations that may have some similarity to known inhibitory molecules. Such analysis has been shown effective in the development of HIV protease inhibitors (Lam, et al. (1994) *Science* 263:380-384; Wlodawer, et al. (1993) *Ann. Rev. Biochem.* 62:543-585; Appelt (1993) *Perspectives in Drug Discovery and Design* 1:23-48; Erickson (1993) *Perspectives in Drug Discovery and Design* 1:109-128). Alternatively, random screening of a small molecule library could lead to inhibitors whose activity may then be analyzed by computer modeling to better determine their effectiveness.

Programs suitable for searching three-dimensional databases include MACCS-3D and ISIS/3D (Molecular Design Ltd, San Leandro, Calif.), ChemDBS-3D (Chemical Design Ltd., Oxford, UK), and Sybyl/3 DB Unity (Tripos Associates, St Louis, Mo.). Programs suitable for compound selection and design include, e.g., DISCO (Abbott Laboratories, Abbott Park, Ill.), Catalyst (Bio-CAD Corp., Mountain View, Calif.), and ChemDBS-3D (Chemical Design Ltd., Oxford, UK).

Compounds which can be screened in accordance with the method of the present invention are generally derived from libraries of agents or compounds. Such libraries can contain either collections of pure agents or collections of agent mixtures. Examples of pure agents include, but are not limited to, proteins, polypeptides, antibodies, antibody fragments, peptides, nucleic acids, oligonucleotides, carbohydrates, lipids, synthetic or semi-synthetic chemicals, and purified natural products. Databases of chemical structures are also available from a number of sources including Cambridge Crystallographic Data Centre (Cambridge, UK) and Chemical Abstracts Service (Columbus, Ohio). De novo design programs include Ludi (Biosym Technologies Inc., San Diego, Calif.), Sybyl (Tripos Associates) and Aladdin (Daylight Chemical Information Systems, Irvine, Calif.).

The invention is described in greater detail by the following non-limiting examples.

Example 1

Materials and Methods

Proline-and-Arginine Rich Peptides. The amino acid sequence of chemically synthesized PR-peptide used the porcine PR39 sequence: $NH_2$-RRRPRPPYLPRPRPPPFFP-PRLPPRI PPGFPPRFPPRFP-COOH (SEQ ID NO:1). Synthetic PR39, PR11 (RRRPRPPYLPR; SEQ ID NO:2), and AAA-PR11 (AAAPRPPYLPR; SEQ ID NO:3) were purchased from C S Bio Inc. (San Carlos, Calif.) or Genemed Biotechnologies, Inc. (South San Francisco, Calif.). All other peptides were obtained from the Tufts Core Facility (Boston, Mass.). All peptides used herein were HPLC-purified and dissolved in phosphate-buffered saline. Peptide concentrations were determined using the molar extinction co-efficient (1280 $M^{-1}$ $cm^{-1}$ at 280 nm) of the single tyrosine residue.

Mutant Peptides. The mutant PR11 peptides synthesized and analyzed herein are listed in Table 2

TABLE 2

| Peptide Name | Mutant Peptide Sequence | SEQ ID NO: |
|---|---|---|
| W12 | RRRPRPPYLPRW | 4 |
| K1 | KRRRPPYLPR | 5 |
| K1E8 | KRRPRPPELPR | 6 |
| K2 | RKRPRPPYLPR | 7 |
| K3 | RRKPRPPYLPR | 8 |
| KKK | KKKPRPPYLPR | 9 |
| A1 | ARRPRPPYLPR | 10 |
| A1E8 | ARRPRPPELPR | 11 |
| A2 | RARPRPPYLPR | 12 |
| A3 | RRAPRPPYLPR | 13 |
| A8W12 | RRRPRPPALPRW | 14 |
| F8W12 | RRRPRPPFLPRW | 15 |
| E8 | RRRPRPPELPR | 16 |
| E8W12 | RRRPRPPELPRW | 17 |
| A4 | RRRARPPYLPR | 18 |
| A5 | RRRPAPPYLPR | 19 |
| A6 | RRRPRAPYLPR | 20 |
| A7 | RRRPRPAYLPR | 21 |
| G9 | RRRPRPPYGPR | 22 |

TABLE 2-continued

| Peptide Name | Mutant Peptide Sequence | SEQ ID NO: |
|---|---|---|
| A10 | RRRPRPPYLAR | 23 |
| A11 | RRRPRPPYLPA | 24 |
| ARA | ARAPRPPYLPR | 25 |
| AAR | AARPRPPYLPR | 26 |
| RAA | RAAPRPPYLPR | 27 |

Determination of Enzymatic Activity. Mammalian (Human) 20s Proteasome was purchased from Boston Biochem (Cambridge, Mass.); substrate, N-succinyl-LLVY-AMC was purchased from SIGMA (St. Louis, Mo.); and negative control, Lactacystin, was purchased from SIGMA. The chymotrypsin-like (ChT-L) peptidase activity was measured using the N-Succinyl-LLVY-AMC substrate (SIGMA) according to known protocols (Gaczynska, et al. (2003) *Biochemistry* 42(29):8663-70). Activity was determined by measuring the amount of a fluorescence observed upon release of the MCA group after a 1 hour incubation at 37° C. in 50 mM sodium phosphate buffer at pH 7.5 containing 0.03% SDS. Inhibition by PR-peptide was measured after a 15-minute pre-incubation at 37° C. of each peptide with 20S proteasome, followed by the addition of the substrate and the one hour incubation.

Cell Culture. Human umbilical vein endothelial cells (HUVEC, Cambrex Bio Science Walkersville, Inc., East Rutherford, N.J.) were cultured in endothelial cell basal medium-2 supplemented with EGM-2 SINGLEQUOTS (Cambrex Bio Science Walkersville, Inc.) and FBS. Confluent HUVEC, passage 3-5, were starved overnight in medium supplemented with 0.5% FBS, 0.25% BSA and incubated with PR peptides (1 µM) for 8 hours in starvation medium.

Total RNA Extraction and Gene Profiling by Microarray. Total RNA extraction was performed using the RNEASY mini kit protocol (QIAGEN, Valencia, Calif.). The quality and quantity of total RNA was determined using RNA 6000 Nano chips (Agilent Technology, Santa Clara, Calif.).

Gene profiling was performed using pathway-specific gene expression array for NF-κB signaling transduction (HS-016.2, SuperArray Bioscience Corp.). A total of 96 cDNA fragments from genes related to NF-κB mediated signal transduction, including: NF-κB/IκB family, NF-κB responsive genes (adhesion molecules, cytokines), extracellular ligands, transmembrane receptors, adaptor proteins, signal transduction kinases, and transcription factors were printed in tetraspot format on 3.8×4.8 cm nylon array membrane. Total RNA (0.5 µg) was reverse-transcribed into cDNA labeled with biotin-dUTP according to the manufacture's protocol. After overnight hybridization at 60° C., array membranes were treated with alkaline phosphate-conjugated streptavidin followed by chemiluminescent alkaline phosphate substrate CDP-star (Applied Biosystems, Foster City, Calif.) and exposed to X-ray film. The data were extracted from raw images using SCANALYSE software (SuperArray, Bioscience Corp.). After background subtraction, the level of gene expression was determined as signal intensity units relative to total array intensity signal. Statistical significant altered genes (PR peptides vs. control) at P values <0.05 were analyzed by Student's t-test, 2-tailed distribution. The data were expressed as fold change PR peptides relative to controls (untreated cells kept in similar conditions).

NMR spectroscopy. One- and two-dimensional solution NMR spectra of PR11 and its alanine mutants were taken in PBS at 7° C. using an 800 MHz NMR BRUKER AVANCE spectrometer fitted with a cryoprobe. Standard pulse programs available within the BRUKER suite of experiments were used with optimization of pulse lengths and power levels. Two-dimensional NMR spectra were recorded in the phase sensitive mode using states-TPPI for quadrature detection in the t1 dimension (Redfield & Kunz (1975) *J. Magn. Res.* 19:250-254; Marion & Wüthrich (1983) *Biochem. Biophys. Res. Commun.* 113:967-974). Solvent suppression for NOESY and TOCSY experiments was achieved using excitation sculpting method with gradients (Hwang & Shaka (1995) *J. Magn. Reson. A* 112:76-80). TOCSY and NOESY spectra were referenced to water proton signal at 280 K. For TOCSY data, recorded using a MLEV-17 mixing scheme (Bax & Davis (1985) *J. Magn. Reson.* 65:355-360), mixing times of 50 and 80 ms were used. NOESY experiments were carried out with 250, 400, and 600 ms; the latter was used in spin system identification and proton assignments. Two-dimensional data were collected with 2048×512 complex data points with 8 scans per increment and a spectral width of 10 ppm in each dimension. All data were processed in FELIX (Accelrys Inc., San Diego, Calif.) using either 60°-shifted sine-squared bell function, or a 30°-shifted sine-squared bell in both dimensions, for resolution enhancement, zero-filled, and Fourier transformed. Face-Lift (Chylla & Markley (1993) *J. Magn. Reson. Series B* 102:148-154) base line correction method was applied to both dimensions. Sequence specific assignments were made using established protocols (Wüthrich (1986) in *NMR of Proteins and Nucleic Acids* John Wiley & Sons, Inc., New York) and various site-specific mutants of PR11. Assignments of the first three residues were confirmed using alanine scanning mutations at these positions.

Structure Calculations. Three-dimensional structures were calculated using simulated annealing, using NOE-based distance restraints and backbone dihedral angles measured from resolution-enhanced NOESY data as described previously (Veeraraghavan, et al. (1998) *Biochem. J.* 332:549-555). The NOE-based distance restraints were classified as strong, medium and weak, corresponding to upper limits of 2.8, 3.4, and 5.0 Å respectively. The torsion angle dynamics protocol of CNS 1.1 (Brunger, et al. (1998) *Acta Crystallogr. D Biol. Crystallogr.* 54 (Pt 5):905-921) was used to calculate 50 structures. These structures were further refined using Cartesian dynamics. The 25 lowest energy structures were used for further analyses. None of the 25 structures violated NOE greater than 0.5 Å and dihedral angles greater than 5°. Structures were analyzed using PROCHECK-NMR (Laskowski, et al. (1996) *J. Biomol. NMR* 8:477-486).

Example 2

20S-Inhibitory Activity of Mutant PR Peptides

The chymotrypsin-like activity of mammalian 20S proteasome is inhibited by the proline-and-arginine-rich peptide, PR39, and its N-terminal fragment, PR11. AAA-PR11, in which the first three arginines are mutated to alanines, is not an inhibitor of 20S. To elucidate amino acids within PR11 that are essential for the 20S inhibiting activity and to establish correlation between the 20S-inhibiting activity and action along the NF-κB pathway, systematic structure-function analyses were conducted. Some peptides in which Tyr8 was mutated to a non-aromatic residue were designed to contain an added $12^{th}$ residue, tryptophan, for ease of peptide quantification. The addition of Trp12 did not significantly alter the PR11 activity in 20S enzymatic activity assays. This indicates that either the Trp12 does not interfere with PR11 interaction with 20S proteasome or that Trp12 provides a hydrophobic contact that might be similar to Pro12 in PR39.

The replacement of any one of the first three arginines of PR11 with lysine altered the activity only slightly and the I50 remained in the range of ~0.5-0.8 µM. Arg→Lys is a conservative replacement and the positive charge on the side chains were retained in each of these mutants. However, replacement of all three arginines with lysines (KKK-PR11) made the peptide less active, increasing $I_{50}$ to 2.7 µM. This indicates that interactions with 20S proteasome may involve not only electrostatic attractive interactions but also hydrogen bonding. Hydrogen-bonding pattern of lysine and arginine are different and this may contribute to the differences in the activity against 20S.

To test which of the arginines must be retained for activity, each arginine was replaced with alanine. These peptides had activities similar to the KKK-PR11 peptide although only one arginine was mutated to alanine, indicating that charge-charge interactions play an important role in recognizing 20S proteasome. Further, to examine whether all three arginines are necessary for the activity or just any two would suffice, pairs of arginines were mutated in the first three residues. Unexpectedly, the $I_{50}$s for double mutants were in between those of single mutations and the triple (AAA-PR11) mutation. Thus, the contribution of the arginines to the 20S inhibiting activity of PR11 is additive.

PR11 contains four prolines, namely, Pro4, Pro6, Pro7, Pro10. Peptides containing Xaa-Pro bonds can exist in multiple conformations because the cyclic nature of the imino acid, proline allows cis and trans isomerization about this bond. Furthermore, populations of peptides that exist in cis conformation depend on the bulkiness of the preceding amino acid. Thus, PR11, with its Pro-Pro and Leu-Pro bonds was expected to be composed of populations in which one or more cis conformers existed. Thus, multiple sets of NMR cross-peaks corresponding to each of these conformers were expected. The NMR spectrum of PR11 showed one set of peaks corresponding to the major conformer at about 80% concentration and at least one minor conformer. In cases where multiple conformers coexist in solution, it is generally difficult to predict, apriori, whether the cis or the trans conformers are the active forms. NMR cross-peaks between the preceding residue's alpha proton, and the alpha or delta protons of prolines are valuable in distinguishing between cis and trans conformers. Alternatively, in cases of significant resonance overlaps, site-specific mutation of prolines can be used. Since other amino acids have very low propensity to adopt the cis configuration, only the trans conformer would prevail in the mutants. To determine whether the active form of PR11 was composed of a cis bond, proline to alanine mutations were analyzed. Pro to Ala mutations of residues 6, 7, or 10 had only a slight effect on PR11 activity and it was concluded that isomerization about the Arg5-Pro6, Pro6-Pro7, or Leu9-Pro10 bonds did not contribute to the observed PR11 activity. Pro4Ala mutant showed increased $I_{50}$ (5 µM). Thus, Pro4 contributes to the 20S inhibiting activity of PR11 by providing structural rigidity or appropriate orientation to residues in the N-terminal half of the molecule.

PR11 contains one aromatic residue, Tyr8. Its Hδ and Hε side chain protons resonate at 7.13 and 6.84 ppm (Table 3).

TABLE 3

| Residue | NH | $H_\alpha$ | $H_\beta$ | Other |
|---|---|---|---|---|
| Arg1 | 8.31 | 3.79 | 1.81 | γCH2, 1.64; δCH2 |
| Arg2 | 8.69 | 4.37 | 1.81 | γCH2, 1.68 m 1.65; δCH2, 3.23 |
| Arg3 | 8.67 | 4.62 | 1.87 | γCH2, 1.76; δCH2, 3.25 |
| Pro4 |  | 4.44 | 2.31, 2.04 | γCH2, 1.88; δCH2, 3.86, 3.67 |
| Arg5 | 8.58 | 4.58 | 1.84 | γCH2, 1.74; δCH2, 3.22 |
| Pro6 |  | 4.69 | 2.36, 2.04 | γCH2, 1.81; δCH2, 3.88, 3.62 |
| Pro7 |  | 4.39 | 2.27, 2.02 | γCH2, 2.11; δCH2, 3.81, 3.67 |
| Tyr8 | 8.09 | 4.56 | 3.06, 2.97 | δCH2, 7.13; εCH2, 6.84 |
| Leu9 | 8.02 | 4.62 | 1.51 | γCH2, 1.51*; δCH3, 0.91 |
| Pro10 |  | 4.35 | 2.31, 2.04 | γCH2, 1.98; δCH2, 3.64, 3.60 |
| Arg11 | 8.04 | 4.14 | 1.85 | γCH2, 1.74, 1.64; δCH2, 3.21 |

$^a$Experimental conditions: PBS, pH 7.40, 280 K.

*Ambiguous assignment.

Nuclear Overhauser Effect (NOE) correlations to the peaks from various residues of PR11 provided unique signatures for wild-type and mutant peptides. For instance, cross-peaks corresponding to a minor conformer(s) in which Hδ resonated at 6.7 ppm disappeared in the Pro7Ala mutant. Furthermore, cross-peaks to Hδ were very weak in the Pro6Ala mutant, and several cross-peaks to the major and minor conformer were missing in the Pro10Ala mutant. These data confirm that Pro7 and, to a lesser extent, Pro6 and Pro10 produce the minor conformers in PR11. In the Pro4Ala mutant, several cross-peaks to the major conformer (Hδ at 6.7 ppm) were weaker or missing, indicating that the Pro4 mutation altered PR11 conformation. Subsequently, it was determined whether the hydrophobic/aromatic group or the side chain hydroxyl was essential for PR11 activity. If the electronegative hydroxyl group were necessary for 20S binding or inhibition, mutation of Tyr8 to Glu would improve PR11 activity, whereas if the aromatic or hydrophobic interactions were more important, mutation to Glu would impair PR11 activity, but mutation to another hydrophobic residue lacking the OH group would leave PR11 activity unaltered. It was found that the Tyr8Glu mutation worsened the $I_{50}$ somewhat (2.4 µM), whereas the double-mutant Lys1Glu8 had a significantly worse $I_{50}$ (6.3 µM). In comparison, Lys1 mutation alone showed an $I_{50}$ of 0.6 µM. A Glu8Trp12 mutant was also designed to determine peptide concentration using the UV absorbance properties of the tryptophan, in mutants lacking tyrosine. This peptide behaved much the same as the Glu8 mutant, indicating that the addition of Trp12 did not significantly alter PR11 activity. To confirm the latter, a control in which Trp12 was added to the normal PR11 was also designed. Again, it was observed that Trp12 did not noticeably alter PR11 activity. The results of Lys1Glu8 mutant indicate that residues 1 and 8 made potentially important contacts with 20S proteasome and that multiple mutations of key residues compound the adverse effects with regard to 20S recognition or inhibition. As for the hydrophobic mutations, Tyr8Ala and Tyr8Phe, both in the background of Trp12, gave $I_{50}$s of 0.034 and 0.715 µM, respectively. Thus, removal of the hydroxyl group did not significantly reduce PR11 activity, whereas shortening the side chain length did. Still, these mutants were better inhibitors of 20S proteasome than the KKK, A1, A2, A3, A4, A5, or E8-containing PR mutants (Table 4). These data show that the presence of a hydrophobic amino acid side chain in position 8 is preferred.

TABLE 4

| PR Peptide | Sequence | SEQ ID NO: | $I_{50}$ (µM) | Error | N | Error |
|---|---|---|---|---|---|---|
| PR39 | RRRPRPPYLPRPRPPPFPPRLPPRIPPGFPPRFPPRFP | 1 | 0.004 | 0.005 | 1.232 | 0.151 |
| W12 | RRRPRPPYLPRW | 4 | 0.006 | 0.019 | 1.171 | 0.161 |
| F8W12 | RRRPRPPFLPRW | 15 | 0.034 | 0.060 | 1.128 | 0.153 |
| G9 | RRRPRPPYGPR | 22 | 0.137 | 0.116 | 1.389 | 0.319 |
| K2 | RKRPRPPYLPR | 7 | 0.543 | 0.156 | 1.093 | 0.264 |
| K1 | KRRRPPYLPR | 5 | 0.595 | 0.186 | 0.933 | 0.258 |
| A11 | RRRPRPPYLPA | 24 | 0.685 | 0.119 | 1.953 | 0.305 |
| A8W12 | RRRPRPPALPRW | 14 | 0.715 | 0.267 | 1.154 | 0.310 |
| A10 | RRRPRPPYLAR | 23 | 0.782 | 0.231 | 1.321 | 0.292 |
| PR11 | RRRPRPPYLPR | 2 | 0.805 | 0.321 | 0.977 | 0.248 |
| K3 | RRKPRPPYLPR | 8 | 0.819 | 0.154 | 1.150 | 0.226 |
| A7 | RRRPRPAYLPR | 21 | 0.851 | 0.220 | 3.921 | 1.259 |
| A6 | RRRPRAPYLPR | 20 | 1.223 | 0.485 | 2.804 | 1.145 |
| E8 | RRRPRPPELPR | 16 | 2.373 | 0.632 | 1.341 | 0.290 |
| E8W12 | RRRPRPPELPRW | 15 | 2.615 | 0.369 | 2.568 | 0.297 |
| A5 | RRRPAPPYLPR | 19 | 2.652 | 0.691 | 3.489 | 0.813 |
| KKK | KKKPRPPYLPR | 9 | 2.714 | 0.916 | 1.177 | 0.337 |
| A2 | RARPRPPYLPR | 12 | 2.767 | 0.709 | 1.636 | 0.330 |
| A1 | ARRPRPPYLPR | 10 | 2.811 | 0.507 | 1.722 | 0.258 |
| A3 | RRAPRPPYLPR | 13 | 3.153 | 0.600 | 1.900 | 0.277 |
| A4 | RRRARPPYLPR | 18 | 4.993 | 0.653 | 1.769 | 0.151 |
| K1E8 | KRRPRPPELPR | 6 | 6.336 | 1.073 | 1.586 | 0.162 |
| ARA | ARAPRPPYLPR | 25 | 11.299 | 3.150 | 1.598 | 0.164 |
| AAR | AARPRPPYLPR | 26 | 14.479 | 8.268 | 1.663 | 0.328 |
| RAA | RAAPRPPYLPR | 27 | 20.130 | 0.122 | 1.447 | 0.122 |
| A1E8 | ARRPRPPELPR | 11 | 49.448 | 12.039 | 2.179 | 0.450 |
| AAA | AAAPRPPYLPR | 3 | >100 | N/A | N/A | N/A |

Another hydrophobic residue, namely, Leu9, follows Tyr8. It was contemplated that Leu9, like Tyr8, was necessary for hydrophobic interactions with 20S proteasome. To test this, Leu9 was replaced with Gly. Gly was chosen over Ala, since Ala was hydrophobic like the original Leu residue. Unexpectedly, the Leu9Gly mutant was fully active, indicating that a hydrophobic residue was not required at position 9 and that Leu9 does not determine the 20S-inhibiting or binding activity of PR11. This finding is unexpected since PR8 (RRRPRPPY; SEQ ID NO:28) does not inhibit 20S activity (Gaczynska, et al. (2003) supra). One explanation is that although Leu9 and Pro10 are not essential for the activity, Arg11 is essential. Therefore, an Arg11Ala mutant was made. This peptide was also quite active with $I_{50}$ for 20S inhibition of 0.685 µM. These results indicate that although any one of the three residues at the C-terminal end may be dispensable, these residues provide orientational or conformational selectivity for appropriate interaction with 20S thereby improving binding affinity. Alternatively, these C-terminal residues are necessary for regulating conformational changes in 20S that are associated with PR11 binding and selective inhibition of 20S activity.

Example 3

PR11 Regulation of NF-κB-Related Gene Expression

NF-κB is a key component of the inflammatory pathway. It has been shown that PR39 acts as an anti-inflammatory agent by inhibiting degradation of IκBα, thereby inhibiting NF-κB activity (Gao, et al. (2000) *J. Clin. Investig.* 106:439-448, Bao, et al. (2001) *Am. J. Physiol. Heart Circ. Physiol.* 281: H2612-H2618). However, the identification of genes that are altered by PR11 and the extent of PR11s effect on genes which regulate the NF-κB signaling pathway have remained unknown. It was posited that the inhibition of IκBα degradation by PR11 might affect the expression of upstream genes regulating the NF-κB pathway activity and that the magnitude of that effect would correspond to the extent of IκBα degradation inhibition by PR11 and its analogs. Hence, using an NF-κB-specific microarray, changes in the expression of genes regulating the NF-κB pathway were investigated in endothelial cells which were induced by PR11 or its mutants.

The expression of 16 genes was significantly affected by PR11 treatment. Table 5 lists the kinase genes which were down-regulated by PR11 and mutants thereof, Table 6 lists the transcription factor and NF-κB family member genes which were down-regulated by PR11 and mutants thereof, Table 7 lists the genes which were up-regulated by PR11 and mutants thereof.

TABLE 5

| | Kinase | | | | | | | | |
|---|---|---|---|---|---|---|---|---|---|
| PR | TAK1 | RIP | TRAF6 | TBK1 | MEKK1 | MEKK2 | MEK4 | JNK1 | P38 MAPK |
| PR11 (n = 4) | −9.2[#] | −10.4[#] | −2.4* | −2.8* | −2.9* | −2.6* | −3.1* | −6.5[#] | −3.6[#] |
| K1 (n = 3) | −23.0[#] | −41.5[#] | −6.6* | −8.1[#] | −8.8* | −4.0* | −14.8[#] | −9.9* | −4.0[#] |
| K2 (n = 3) | −2.1* | −2.8* | −2.5 | −4.6[#] | −5.3* | −1.7 | −9.3[#] | −3.1 | −1.4 |

TABLE 5-continued

| | Kinase | | | | | | | | |
|---|---|---|---|---|---|---|---|---|---|
| PR | TAK1 | RIP | TRAF6 | TBK1 | MEKK1 | MEKK2 | MEK4 | JNK1 | P38 MAPK |
| K3 (n = 3) | -3.1# | -2.4* | -1.7 | -1.8* | -3.2 | -1.9# | -3.1* | -3.2* | -1.7* |
| KKK (n = 3) | -2.9* | -2.6 | -1.3 | -1.8# | -2.0 | -1.5 | -2.8* | -2.5 | -1.3 |
| A1 (n = 3) | -1.4* | -0.9 | -1.1 | -1.4* | -1.0 | -1.2 | -0.9 | -1.1 | -1.1 |
| A2 (n = 3) | -0.8 | -1.1 | -1.1 | -1.3 | -1.8 | -0.9 | -1.9 | -1.5 | -0.9 |
| A3 (n = 3) | -3.3* | -3.0* | -1.4 | -2.1* | -1.9 | -2.1* | -2.7* | -2.6 | -1.9* |
| AAA (n = 4) | -1.0 | -1.0 | -1.0 | -1.0 | -1.0 | -1.0 | -1.0 | -1.2 | -1.0 |
| W12 (n = 3) | -2.0# | -5.5* | -3.1* | -4.7# | -4.6* | -2.4# | -4.0# | -5.3* | -2.5# |
| E8W12 (n = 3) | -1.2 | -1.5 | -1.2 | -1.6* | -1.7 | -1.1 | -2.4* | -1.8 | -1.1 |
| E8 (n = 4) | -1.7* | -3.6* | -1.2 | -2.3# | -1.0 | -1.3 | -1.2 | -1.2 | -1.5 |
| K1E8 (n = 3) | -2.4# | -3.3* | -5.5* | -3.6# | -1.4 | -3.0# | -1.9* | -2.2 | -2.6# |
| A1E8 (n = 3) | -1.8 | -10.4# | -1.6 | -2.0# | -0.8 | -1.2 | -1.2 | -1.5 | -1.6 |

*<0.05,
<0.01 PR-peptide vs. control (untreated cells kept in similar conditions).

TABLE 6

| | Transcription Factor | | NF-κB Family | |
|---|---|---|---|---|
| PR | CREB1 | ATF2 | NF-κB1 | NF-κB2 |
| PR11 (n = 4) | -2.1* | -2.1* | -4.1* | -3.3# |
| K1 (n = 3) | -5.9# | -3.7# | -3.8* | -1.8* |
| K2 (n = 3) | -2.6 | -2.0# | -2.1 | -1.5 |
| K3 (n = 3) | -1.6 | -1.6* | -2.2 | -1.2 |
| KKK (n = 3) | -1.3 | -1.3 | -2.4 | -1.4 |
| A1 (n = 3) | -1.4 | -1.4* | -1.1 | -1.1 |
| A2 (n = 3) | -1.4 | -1.2 | -1.2 | -0.8 |
| A3 (n = 3) | -1.3 | -1.3 | -2.0 | -1.4 |
| AAA (n = 4) | -1.0 | -1.0 | -1.3 | -1.0 |
| W12 (n = 3) | -1.6 | -2.7# | -2.6 | -1.9* |
| E8W12 (n = 3) | -1.5 | -1.8* | -1.6 | -1.3 |
| E8 (n = 4) | -1.9 | -1.6* | -1.7 | -1.4 |
| K1E8 (n = 3) | -5.0# | -2.6# | -1.9 | -2.3* |
| A1E8 (n = 3) | -2.2* | -1.5* | -1.6 | -3.5* |

*<0.05,
<0.01 PR-peptide vs. control (untreated cells kept in similar conditions).

TABLE 7

| PR | Receptor RANK | Kinase AKT1 | Transcription Factor ELK3 |
|---|---|---|---|
| PR11 (n = 4) | 1.5* | 3.0* | 1.9* |
| K1 (n = 3) | 1.5 | 1.8* | 1.8# |
| K2 (n = 3) | 1.1 | 1.6 | 1.5* |
| K3 (n = 3) | 1.7* | 1.7 | 1.4# |
| KKK (n = 3) | 1.2 | 1.7 | 1.4# |
| A1 (n = 3) | 1.2 | 1.3 | 0.9 |
| A2 (n = 3) | 1.4 | 1.4 | 1.0 |
| A3 (n = 3) | 1.7* | 1.7 | 1.3* |
| AAA (n = 4) | 1.1 | 0.9 | 1.0 |
| W12 (n = 3) | 2.1# | 2.5# | 1.3# |
| E8W12 (n = 3) | 1.8# | 1.8* | 1.0 |
| E8 (n = 4) | 1.5 | 0.8 | ^-1.8# |
| K1E8 (n = 3) | 0.7 | 0.6 | ^-1.9# |
| A1E8 (n = 3) | 1.3 | 0.8 | ^-1.9# |

*<0.05,
<0.01 PR-peptide vs. control (untreated cells kept in similar conditions),
^gene up-regulated by PR11 found down-regulated by mutant.

The changes included a reduced expression of various MAP kinases and associated factors including TAK1 (also known as MAP3K7, Mitogen-Activated Protein Kinase Kinase Kinase 7, or Transforming growth factor β Activated Kinase 1), RIP1 (Receptor (TNFRSF)-Interacting serine-threonine Protein kinase 1), TRAF6 (Tumor necrosis factor Receptor-Associated Factor 6), TBK1 (TANK-binding kinase 1), MEKK1 (Mitogen-Activated Protein Kinase Kinase Kinase 1), MEKK2 (Mitogen-Activated Protein Kinase Kinase Kinase 2), MEK4 (Mitogen-Activated Protein Kinase Kinase 4 or JNK activating kinase 1), JNK1 (Mitogen-Activated Protein Kinase 8 or stress-activated protein kinase JNK1), p38 MAPK (Mitogen-Activated Protein Kinase 14); transcription factors involved in IKK regulation and downstream transcription factors including CREB1 (cAMP Responsive Element Binding protein 1 transcription factor) and ATF2 (Activating Transcription Factor 2); as well as members of the NF-κB family including NF-κB1 (Nuclear Factor of Kappa light polypeptide gene enhancer in B-cells 1 (p105)) and NF-κB2 (Nuclear Factor of Kappa polypeptide gene enhancer in B-cells (p49/p100)). Unexpectedly, there was an increase in expression of the TNF receptor family member RANK (Tumor Necrosis Factor Receptor Super-Family, member 11a, activator of NFκB), AKT1 (V-akt murine thymoma viral oncogene homolog 1 or protein kinase B) and ELK3 (ETS-domains protein (SRF accessory protein 2)) genes, possibly to compensation for perceived reduction in NF-κB activation. These effects were taken as the reference point in examining the effects of various PR11 mutants on regulation of expression of NF-κB cascade genes.

K1-, K2-, K3-, and KKK-PR11 mutants. Among lysine mutants (Arg1Lys, Arg2Lys, Arg3Lys, and Arg1,2,3→Lys1, 2,3), the activity of K1-PR11 was the same as PR11. However, expression levels of several MAP kinases was dramatically reduced (e.g., TAK1: 23-fold, RIP: 41-fold, TBK1: 8-fold, MEK4: 15-fold) (Table 5) and overall K1-PR11 inhibitory effect was higher than PR11 (FIG. 1). K2-PR11 and K3-PR11 mutants were less active than K1-PR11 with only 6 and 8 significantly reduced genes, respectively (Tables 5 and 6), but overall activity was not significantly different than PR11 (FIG. 1). KKK-PR11 mutant activity showed the lowest inhibitory effect in this series with only 3 genes significantly reduced (TAK1, TBK1, and MAK4) (Table 5, FIG. 1). This indicates that the replacement of first three arginine residues with another positively charged amino acid, lysine, was relatively well-tolerated. It also revealed that although their side chain charges were similar, Lys was preferable at position 1 of PR11.

A1-, A2-, A3-, and AAA-PR11 mutants. Arg1Ala and Arg2Ala dramatically reduced PR11 activity compared to PR11 (FIG. 1). A3-PR11 was more active than A1-PR11 and A2-PR11, down-regulating 5 of the 13 genes (FIG. 1). However, substituting the first 3 Arg residues with Ala completely abolished PR11 activity (FIG. 1). These data show that a positively charged residue at the N-terminus is necessary for PR11 activity.

W12-, E8W12-, E8-, K1E8-, A1E8-PR11 mutants induced gene profiling. Trp12 mutant activity was similar with that of PR11 (FIG. 1). Glu8Trp12, Glu8, and Ala1Glu8 showed a reduced activity compared with PR11 or Trp12, with the expression levels of only 3-5 genes reduced, namely, TBK1, ATF2, MEK4, TAK1, RIP1, or CREB1 (FIG. 1). These data demonstrated that a negatively charged residue at position 8 was not well-tolerated. Activity of the Lys1Glu8 mutant was higher than that of Glu8 or Ala1Glu8 (FIG. 1), consistent with increased activity afforded to PR11 by the lone replacement of Arg1 with Lys.

Overall, results from these mutants established the requisites for PR11 to be able to act along the NF-κB pathway. These are: inclusion of two positively charged residues at the N-terminus and exclusion of negatively charged residues at position 8. These findings parallel the findings on the 20S proteasome inhibiting activity of PR11, indicating that the in situ effects of PR11 stem largely from its ability to inhibit proteasomes.

Example 4

NMR Structure of PR11

PR11 contains five arginines and four prolines; severe overlap in the beta and gamma proton chemical shifts of these residues presented a significant challenge to spin system identification, resonance assignment, and conformational analysis by NMR. To overcome these challenges, TOCSY and NOESY spectra of wild-type and site-specifically mutated PR11 were used to identify each spin system and to make sequence-specific assignments (Table 3).

Sequential connectivities between of alpha proton ($H_\alpha$) of the any given residue (i) and the amide proton (HN) of the following residue (i+1) were used to establish residue specific assignments. These NOE contacts were not observed for the first three arginines, presumably due to fast relaxation. The intervening Pro residues lack a backbone amide proton, and hence, the connectivity was broken four times. Also, the presence of prolines allows PR11 to exist in multiple conformations, due to cis-trans isomerization about each Xaa-Pro bond. Correspondingly, more than the expected 7 backbone amide protons were observed in the NMR spectra and amide protons of Arginine 5 and Leucine 9 each resonated at two distinct chemical shifts. Weak NOE cross-peaks were observed between $C^\alpha H$ (i) to $C^\alpha H$ (i+1), indicating the presence of minor conformers containing Xxx-Pro cis bonds. Despite these difficulties, unambiguous and sequence-specific assignment of PR11 was possible through the identification of strong NOE cross peak between $C^\alpha H$ (i) to Pro $C^\delta H_2$ (i+1). These strong NOEs also confirmed that the major conformer of the peptide was composed predominantly of the trans configuration.

Chemical shift index (CSI) analysis is a useful first step in identifying regions of proteins that contain regular secondary structural elements such as alpha helices or beta strands. In general, small peptides like PR11 do not contain such regular secondary structural elements. In the instant case, the alpha proton chemical shifts of PR11 deviated little from random coil values excepted due to local sequence when a residue was preceded by proline. However, since mutational results indicated the need for amino acids 1-5 and 8 in PR11 activity, and because the peptide was likely to be relatively rigid due to the presence of four prolines, the structure of PR11 was determined.

Structure elucidation for small peptides involves predominantly short and medium range NOEs frequently involving immediate neighbors of a residue. Long range NOEs are only observed when distant portions of a polypeptide are spatially proximal (within ~5 Å). Further, strong NOEs are expected between $C_\alpha H(i)$ and NH(i+1) whereas NOEs are relatively weak or absent between NH(i) and NH(i+1). The amide region of the NOESY spectrum of PR11 showed that NOEs between amides of adjacent residues were observed only for Tyr8 and Leu9. This was because the amide chemical shifts of these two residues were sufficiently different to produce a cross-peak away from the diagonal because these protons were spatially close enough to produce a NOE that was strong enough to be observed over the noise level. In addition, weak NOEs were detected between the amide protons of Leu9 and the $C_5H$ ring proton of Tyr8, again, indicating the spatial proximity of these residues.

A NMR-assisted model of the three-dimensional structure of PR11 was calculated using NOE-derived distances (99 short-range and 38 medium-range NOEs) and backbone dihedral angles for residues Arg2, Arg3, Arg5, Tyr8, Leu9, and Arg11 (Wang, et al. (1997) *J. Biomol. NMR* 10:373-382). The root-mean-squared distance (RMSD) for the superimposition of backbone alpha carbon atoms of individual models, in the bundle of structures, on to the averaged structure was 1.87 Å. The backbone and side chain orientations of Pro4 and Tyr8 were relatively well-defined compared to those of the first three arginines that did not show any NOEs. This model indicates a tendency for Arg2, Arg5, and Tyr8 to point toward one direction, whereas Arg1 and Arg3 were oriented away. The Arg3-Pro4 peptide bond provides rigidity to the N-terminal half of the peptide, while remaining prolines and contacts to Tyr8 side chain provide rigidity to rest of the peptide. The high rigidity of PR11 due to several prolines, together with the mutational effects of PR11 on 20S activity, indicates that this structural model is representative of the 20S bound conformation of PR11.

What is claimed is:

1. An isolated mutant proline-and-arginine-rich (PR) peptide, wherein said peptide is 11 amino acid residues in length, has a hydrophobic amino acid residue at position eight, and has one to three amino acid substitutions in the amino acid sequence set forth in SEQ ID NO:2, wherein at least one of the amino acid residues at position one, two, or three is positively charged and wherein said peptide exhibits an increase in activity to inhibit 20S proteosome activity compared to the PR peptide of SEQ ID NO:2.

2. An isolated mutant proline-and-arginine-rich (PR) peptide consisting of 12 amino acid residues in length, said peptide having a C-terminal tryptophan, a hydrophobic amino acid residue at position eight, and having one to three amino acid substitutions in the amino acid sequence set forth in SEQ ID NO:2, wherein at least one of the amino acid residues at position one, two, or three is positively charged and wherein said peptide exhibits an increase in activity to inhibit 20S proteasome activity compared to the PR peptide of SEQ ID NO:2.

3. The isolated mutant PR peptide of claim 1, wherein at least two of the amino acid residues at positions one, two, or three are positively charged and the amino acid residue at position eight is not negatively charged.

4. The isolated mutant PR peptide of claim 1, wherein the amino acid residue at position four is proline.

5. An isolated mutant PR peptide consisting of the amino acid sequence set forth in SEQ ID NO:4.

6. An isolated mutant PR peptide consisting of the amino acid sequence set forth in SEQ ID NO:5.

7. A method for inhibiting mammalian 20S proteasome activity comprising contacting a cell with the mutant PR peptide of claim 3 thereby inhibiting 20S proteasome activity in the cell.

8. A method for inhibiting mammalian 20S proteasome activity comprising contacting a cell with the mutant PR peptide of claim 5 thereby inhibiting 20S proteasome activity in the cell.

9. A method for inhibiting mammalian 20S proteasome activity comprising contacting a cell with the mutant PR peptide of claim 6 thereby inhibiting 20S proteasome activity in the cell.

* * * * *

SEQUENCE LISTING

<160> NUMBER OF SEQ ID NOS: 31

<210> SEQ ID NO 1
<211> LENGTH: 39
<212> TYPE: PRT
<213> ORGANISM: Sus scrofa

<400> SEQUENCE: 1

Arg Arg Arg Pro Arg Pro Pro Tyr Leu Pro Arg Pro Arg Pro Pro Pro
1               5                   10                  15

Phe Phe Pro Pro Arg Leu Pro Pro Arg Ile Pro Pro Gly Phe Pro Pro
            20                  25                  30

Arg Phe Pro Pro Arg Phe Pro
        35

<210> SEQ ID NO 2
<211> LENGTH: 11
<212> TYPE: PRT
<213> ORGANISM: Sus scrofa

<400> SEQUENCE: 2

Arg Arg Arg Pro Arg Pro Pro Tyr Leu Pro Arg
1               5                   10

<210> SEQ ID NO 3
<211> LENGTH: 11
<212> TYPE: PRT
<213> ORGANISM: Artificial Sequence
<220> FEATURE:
<223> OTHER INFORMATION: Synthetic peptide

<400> SEQUENCE: 3

Ala Ala Ala Pro Arg Pro Pro Tyr Leu Pro Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide

<400> SEQUENCE: 4

Arg Arg Arg Pro Arg Pro Pro Tyr Leu Pro Arg Trp
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic peptide

<400> SEQUENCE: 5

Lys Arg Arg Arg Pro Pro Tyr Leu Pro Arg
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic peptide

<400> SEQUENCE: 6

```
Lys Arg Arg Pro Arg Pro Pro Glu Leu Pro Arg
1               5                   10
```

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide

<400> SEQUENCE: 7

```
Arg Lys Arg Pro Arg Pro Pro Tyr Leu Pro Arg
1               5                   10
```

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide

<400> SEQUENCE: 8

```
Arg Arg Lys Pro Arg Pro Pro Tyr Leu Pro Arg
1               5                   10
```

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide

<400> SEQUENCE: 9

```
Lys Lys Lys Pro Arg Pro Pro Tyr Leu Pro Arg
1               5                   10
```

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10

```
Ala Arg Arg Pro Arg Pro Pro Tyr Leu Pro Arg
1               5                   10
```

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide

<400> SEQUENCE: 11

```
Ala Arg Arg Pro Arg Pro Pro Glu Leu Pro Arg
1               5                   10
```

<210> SEQ ID NO 12
<211> LENGTH: 11
<212> TYPE: PRT
<213> ORGANISM: Artificial Sequence
<220> FEATURE:
<223> OTHER INFORMATION: Synthetic peptide

<400> SEQUENCE: 12

```
Arg Ala Arg Pro Arg Pro Pro Tyr Leu Pro Arg
```

```
1               5                   10
```

<210> SEQ ID NO 13
<211> LENGTH: 11
<212> TYPE: PRT
<213> ORGANISM: Artificial Sequence
<220> FEATURE:
<223> OTHER INFORMATION: Synthetic peptide

<400> SEQUENCE: 13

```
Arg Arg Ala Pro Arg Pro Pro Tyr Leu Pro Arg
1               5                   10
```

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide

<400> SEQUENCE: 14

```
Arg Arg Arg Pro Arg Pro Pro Ala Leu Pro Arg Trp
1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide

<400> SEQUENCE: 15

```
Arg Arg Arg Pro Arg Pro Pro Phe Leu Pro Arg Trp
1               5                   10
```

<210> SEQ ID NO 16
<211> LENGTH: 11
<212> TYPE: PRT
<213> ORGANISM: Artificial Sequence
<220> FEATURE:
<223> OTHER INFORMATION: Synthetic peptide

<400> SEQUENCE: 16

```
Arg Arg Arg Pro Arg Pro Pro Glu Leu Pro Arg
1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide

<400> SEQUENCE: 17

```
Arg Arg Arg Pro Arg Pro Pro Glu Leu Pro Arg Trp
1               5                   10
```

<210> SEQ ID NO 18
<211> LENGTH: 11
<212> TYPE: PRT
<213> ORGANISM: Artificial Sequence
<220> FEATURE:
<223> OTHER INFORMATION: Synthetic peptide

<400> SEQUENCE: 18

```
Arg Arg Arg Ala Arg Pro Pro Tyr Leu Pro Arg
1               5                   10
```

```
<210> SEQ ID NO 19
<211> LENGTH: 11
<212> TYPE: PRT
<213> ORGANISM: Artificial Sequence
<220> FEATURE:
<223> OTHER INFORMATION: Synthetic peptide

<400> SEQUENCE: 19

Arg Arg Arg Pro Ala Pro Pro Tyr Leu Pro Arg
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic peptide

<400> SEQUENCE: 20

Arg Arg Arg Pro Arg Ala Pro Tyr Leu Pro Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide

<400> SEQUENCE: 21

Arg Arg Arg Pro Arg Pro Ala Tyr Leu Pro Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide

<400> SEQUENCE: 22

Arg Arg Arg Pro Arg Pro Pro Tyr Gly Pro Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide

<400> SEQUENCE: 23

Arg Arg Arg Pro Arg Pro Pro Tyr Leu Ala Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide

<400> SEQUENCE: 24

Arg Arg Arg Pro Arg Pro Pro Tyr Leu Pro Ala
1               5                   10

<210> SEQ ID NO 25
```

```
<211> LENGTH: 11
<212> TYPE: PRT
<213> ORGANISM: Artificial Sequence
<220> FEATURE:
<223> OTHER INFORMATION: Synthetic peptide

<400> SEQUENCE: 25

Ala Arg Ala Pro Arg Pro Pro Tyr Leu Pro Arg
1               5                   10

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide

<400> SEQUENCE: 26

Ala Ala Arg Pro Arg Pro Pro Tyr Leu Pro Arg
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide

<400> SEQUENCE: 27

Arg Ala Ala Pro Arg Pro Pro Tyr Leu Pro Arg
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Arg Arg Arg Pro Arg Pro Pro Tyr
1               5

<210> SEQ ID NO 29
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa is absent or lysine
<220> FEATURE:
<221> NAME/KEY: MISC_FEATURE
<222> LOCATION: (2)..(4)
<223> OTHER INFORMATION: Xaa is any amino acid residue with the proviso
      that at least one of Xaa2, Xaa3, or Xaa4 is a positively charged
      amino acid residue
<220> FEATURE:
<221> NAME/KEY: MISC_FEATURE
<222> LOCATION: (8)..(8)
<223> OTHER INFORMATION: Xaa is any amino acid residue
<220> FEATURE:
<221> NAME/KEY: MISC_FEATURE
<222> LOCATION: (9)..(9)
<223> OTHER INFORMATION: Xaa is not a negatively charged amino acid
      residue.
<220> FEATURE:
<221> NAME/KEY: MISC_FEATURE
<222> LOCATION: (10)..(11)
<223> OTHER INFORMATION: Xaa denotes any amino acid residue.
```

```
<220> FEATURE:
<221> NAME/KEY: MISC_FEATURE
<222> LOCATION: (12)..(12)
<223> OTHER INFORMATION: Xaa is absent or any amino acid residue.
<220> FEATURE:
<221> NAME/KEY: MISC_FEATURE
<222> LOCATION: (13)..(13)
<223> OTHER INFORMATION: Xaa is absent or tryptophan.

<400> SEQUENCE: 29

Xaa Xaa Xaa Xaa Pro Arg Pro Xaa Xaa Xaa Xaa Xaa
1               5                   10

<210> SEQ ID NO 30
<211> LENGTH: 130
<212> TYPE: PRT
<213> ORGANISM: Sus scrofa

<400> SEQUENCE: 30

Met Glu Thr Gln Arg Ala Ser Leu Cys Leu Gly Arg Trp Ser Leu Trp
1               5                   10                  15

Leu Leu Leu Leu Gly Leu Val Val Pro Ser Ala Ser Ala Gln Ala Leu
                20                  25                  30

Ser Tyr Arg Glu Ala Val Leu Arg Ala Val Asp Arg Leu Asn Glu Gln
            35                  40                  45

Ser Ser Glu Ala Asn Leu Tyr Arg Leu Leu Glu Leu Asp Gln Pro Pro
        50                  55                  60

Lys Ala Asp Glu Asp Pro Gly Thr Pro Lys Pro Val Ser Phe Thr Val
65                  70                  75                  80

Lys Glu Thr Val Cys Pro Arg Pro Thr Arg Gln Pro Pro Glu Leu Cys
                85                  90                  95

Asp Phe Lys Glu Asn Gly Arg Val Lys Gln Cys Val Gly Thr Val Thr
            100                 105                 110

Leu Asn Pro Ser Ile His Ser Leu Asp Ile Ser Cys Asn Glu Ile Gln
        115                 120                 125

Ser Val
    130

<210> SEQ ID NO 31
<211> LENGTH: 101
<212> TYPE: PRT
<213> ORGANISM: Sus scrofa

<400> SEQUENCE: 31

Gln Ala Leu Ser Tyr Arg Glu Ala Val Leu Arg Ala Val Asp Arg Leu
1               5                   10                  15

Asn Glu Gln Ser Ser Glu Ala Asn Leu Tyr Arg Leu Leu Glu Leu Asp
                20                  25                  30

Gln Pro Pro Lys Ala Asp Glu Asp Pro Gly Thr Pro Lys Pro Val Ser
            35                  40                  45

Phe Thr Val Lys Glu Thr Val Cys Pro Arg Pro Thr Arg Gln Pro Pro
        50                  55                  60

Glu Leu Cys Asp Phe Lys Glu Asn Gly Arg Val Lys Gln Cys Val Gly
65                  70                  75                  80

Thr Val Thr Leu Asn Pro Ser Ile His Ser Leu Asp Ile Ser Cys Asn
                85                  90                  95

Glu Ile Gln Ser Val
            100
```